US010006976B2

(12) United States Patent  
Ishihara et al.

(10) Patent No.: US 10,006,976 B2  
(45) Date of Patent: Jun. 26, 2018

(54) RADIO FREQUENCY COIL UNIT AND MAGNETIC RESONANCE IMAGING APPARATUS

(71) Applicant: TOSHIBA MEDICAL SYSTEMS CORPORATION, Otawara-shi, Tochigi (JP)

(72) Inventors: Takahiro Ishihara, Tochigi (JP); Sadanori Tomiha, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 649 days.

(21) Appl. No.: 14/631,199

(22) Filed: Feb. 25, 2015

(65) Prior Publication Data

US 2015/0168515 A1    Jun. 18, 2015

Related U.S. Application Data

(63) Continuation of application No. PCT/JP2013/070908, filed on Aug. 1, 2013.

(30) Foreign Application Priority Data

Aug. 29, 2012  (JP) .................................. 2012-188919

(51) Int. Cl.
*G01R 33/36* (2006.01)
*A61B 5/055* (2006.01)

(52) U.S. Cl.
CPC .......... *G01R 33/3685* (2013.01); *A61B 5/055* (2013.01)

(58) Field of Classification Search
CPC ........................ H01F 5/00; H01F 27/00–27/36
(Continued)

(56) References Cited

U.S. PATENT DOCUMENTS 5,420,537 A * 5/1995 Weedon .................. H03F 3/193  
330/251  
7,282,915 B2 * 10/2007 Giaquinto .......... G01R 33/3415  
324/318

(Continued)

FOREIGN PATENT DOCUMENTS

JP    10-314138    12/1998  
JP    2005-021325   1/2005  
(Continued)

OTHER PUBLICATIONS

Non-English International Search Report including Written Opinion of the ISA for PCT/JP2013/070908 dated Aug. 27, 2013, five pages.  
(Continued)

*Primary Examiner* — Tuyen Nguyen  
(74) *Attorney, Agent, or Firm* — Nixon & Vanderhye P.C.

(57) ABSTRACT

According to one embodiment, a radio frequency coil unit includes cables, radio frequency coil elements and balun circuits. The cables correspond to channels. The radio frequency coil elements are directly or indirectly connected to the cables. The balun circuits suppress an influence of an unbalanced current flowing into partial radio frequency coil elements out of the radio frequency coil elements. A part of the cables pass through at least one of the balun circuits in contact with or in non-contact with at least one of the balun circuits.

19 Claims, 8 Drawing Sheets

(58) Field of Classification Search
USPC .......... 336/65, 180–184, 200, 220–223, 232
See application file for complete search history.

(56) References Cited

U.S. PATENT DOCUMENTS 8,547,102 B2 * 10/2013 Nozaki ............ G01R 33/34015
324/318
2011/0267061 A1   11/2011 Taracila et al.

FOREIGN PATENT DOCUMENTS

JP   2010-125050   6/2010
JP   2011-172647   9/2011

OTHER PUBLICATIONS

Notification of Transmittal of Translation of the International Preliminary Report on Patentability in PCT/JP2013/070908 dated Mar. 12, 2015.
H. Fujita et al., "An 8-Channel Body Array Coil for Abdominal Parallel Imaging at 3.0T," Proceedings of International Society for Magnetic Resonance in Medicine [CD-ROM], 2004, p. 2384.
CN Office Action dated Jun. 30, 2015 in in CN 201380001254.9.

* cited by examiner

RADIO FREQUENCY COIL UNIT AND MAGNETIC RESONANCE IMAGING APPARATUS

CROSS REFERENCES TO RELATED APPLICATIONS

This is a continuation of Application PCT/JP2013/70908, filed on Aug. 1, 2013.

This application is based upon and claims the benefit of priority from Japanese Patent Application No. 2012-188919, filed on Aug. 29, 2012; the entire contents of which are incorporated herein by reference.

FIELD

Embodiments described herein relate generally to an RF (radio frequency) coil unit and an MRI (magnetic resonance imaging) apparatus.

BACKGROUND

The MRI apparatus is an image diagnostic apparatus which magnetically excites nuclear spin of an object set in a static magnetic field with an RF signal having the Larmor frequency and reconstructs an image based on MR (magnetic resonance) signals generated due to the excitation.

Into cables of RF coils used in an MRI apparatus, unbalanced currents received from a transmission RF coil and surrounding electric circuits flow. These unbalanced currents can cause a breakage of a circuit element in an RF transceiver system or a degradation in an image quality. Since plural RF coils are usually used in an MRI apparatus, the unbalanced currents are generated in each of the cables connected to the RF coils.

Accordingly, a balun circuit is conventionally connected with cables of RF coils in order to inhibit an influence of the unbalanced currents. The balun circuit has a cylindrical structure. Then, composite cables, in which signal lines and a power source line are bundled, pass through the inside of the balun circuit. In recent years, an MRI apparatus has plural balun circuits in an RF transceiver system and bundled composite cables pass a common balun circuit multiple times.

PRIOR TECHNICAL LITERATURE

[Patent literature 1] JPA 2011-172647

When an unbalanced current flows into a cable connected to an RF coil, the unbalanced current in a balun circuit attenuates and changes into heat. Therefore, installed balun circuits generate heat respectively. However, the balun circuits do not generate heat equally, but a small number of balun circuits generate heat extremely in many cases. This is because an electrical load is applied to a specific balun circuit locally.

Accordingly, an object of the present invention is to provide an RF coil unit and a magnetic resonance imaging apparatus which can put electrical loads on balun circuits, for inhibiting influence by unbalanced currents, more equally.

DETAILED DESCRIPTION

In general, according to one embodiment, a radio frequency coil unit includes cables, radio frequency coil elements and balun circuits. The cables correspond to channels. The radio frequency coil elements are directly or indirectly connected to the cables. The balun circuits suppress an influence of an unbalanced current flowing into partial radio frequency coil elements out of the radio frequency coil elements. A part of the cables pass through at least one of the balun circuits in contact with or in non-contact with at least one of the balun circuits.

Further, according to another embodiment, a magnetic resonance imaging apparatus includes the above mentioned radio frequency coil unit and an imaging system. The imaging system is configured to perform magnetic resonance imaging using the radio frequency coil unit.

A radio frequency coil unit and a magnetic resonance imaging apparatus according to embodiments of the present invention will be described with reference to the accompanying drawings.

First Embodiment

Figure 1:
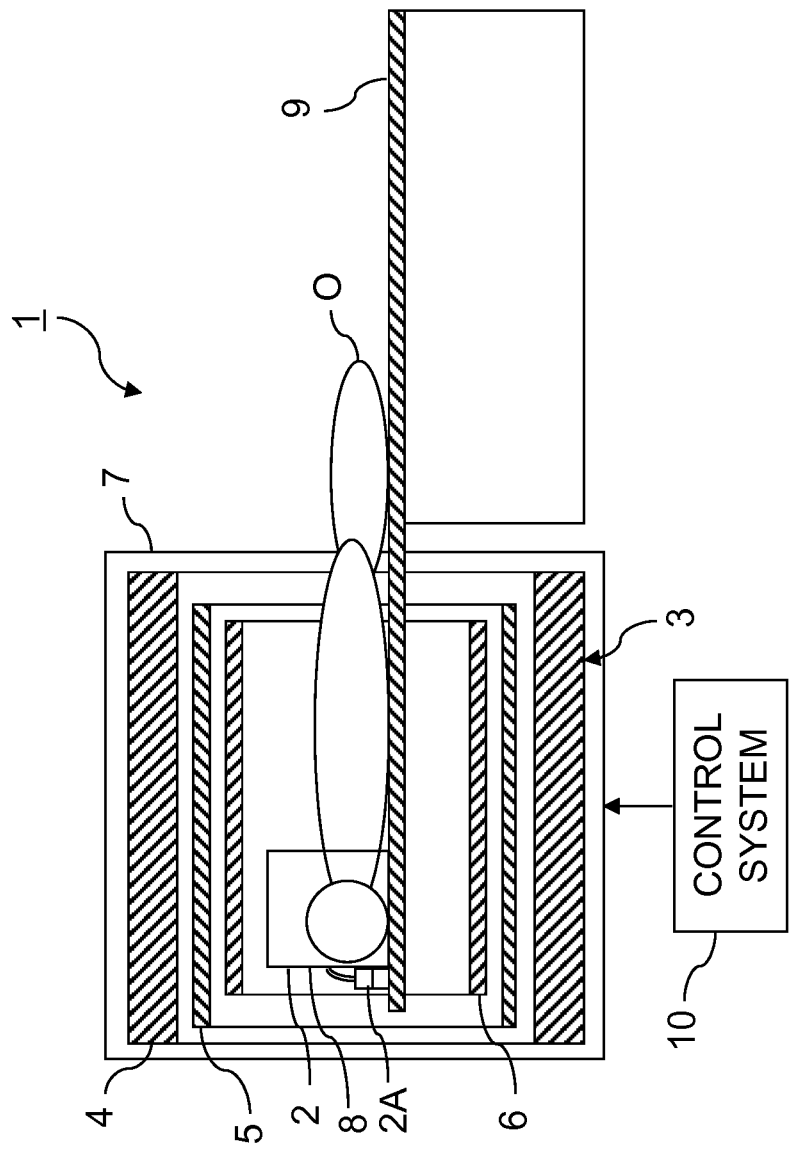
FIG. 1 is a structural view showing an RF coil unit and a magnetic resonance imaging apparatus according to the first embodiment of the present invention.

FIG. 1 is a structural view showing an RF coil unit and a magnetic resonance imaging apparatus according to the first embodiment of the present invention.

A magnetic resonance imaging apparatus 1 is configured by an imaging system 3 with which an RF coil unit 2 is connected. The imaging system 3 is a system which performs MR imaging of an object O using the RF coil unit 2. For that purpose, the imaging system 3 includes a gantry 7, RF coils 8 for receiving MR signals, a bed 9, and a control system 10. A static magnetic field magnet 4, a gradient coil 5, and a WBC (whole body coil) 6 for transmitting RF signals are coaxially built in the gantry 7.

The RF coil unit 2 can be used as one or both of a transmission RF coil for RF signals and a reception RF coil 8 for MR signals. Therefore, the WBC 6 may be the RF coil unit 2. Alternatively, the RF coil unit 2 may be connected to the imaging system 3 as an RF coil for locally transmitting RF signals other than the WBC 6. Note that, FIG. 1 shows an example of attaching the RF coil unit 2 to the imaging system 3 through a connector 2A as an RF coil 8 for receiving MR signals.

Figure 2:
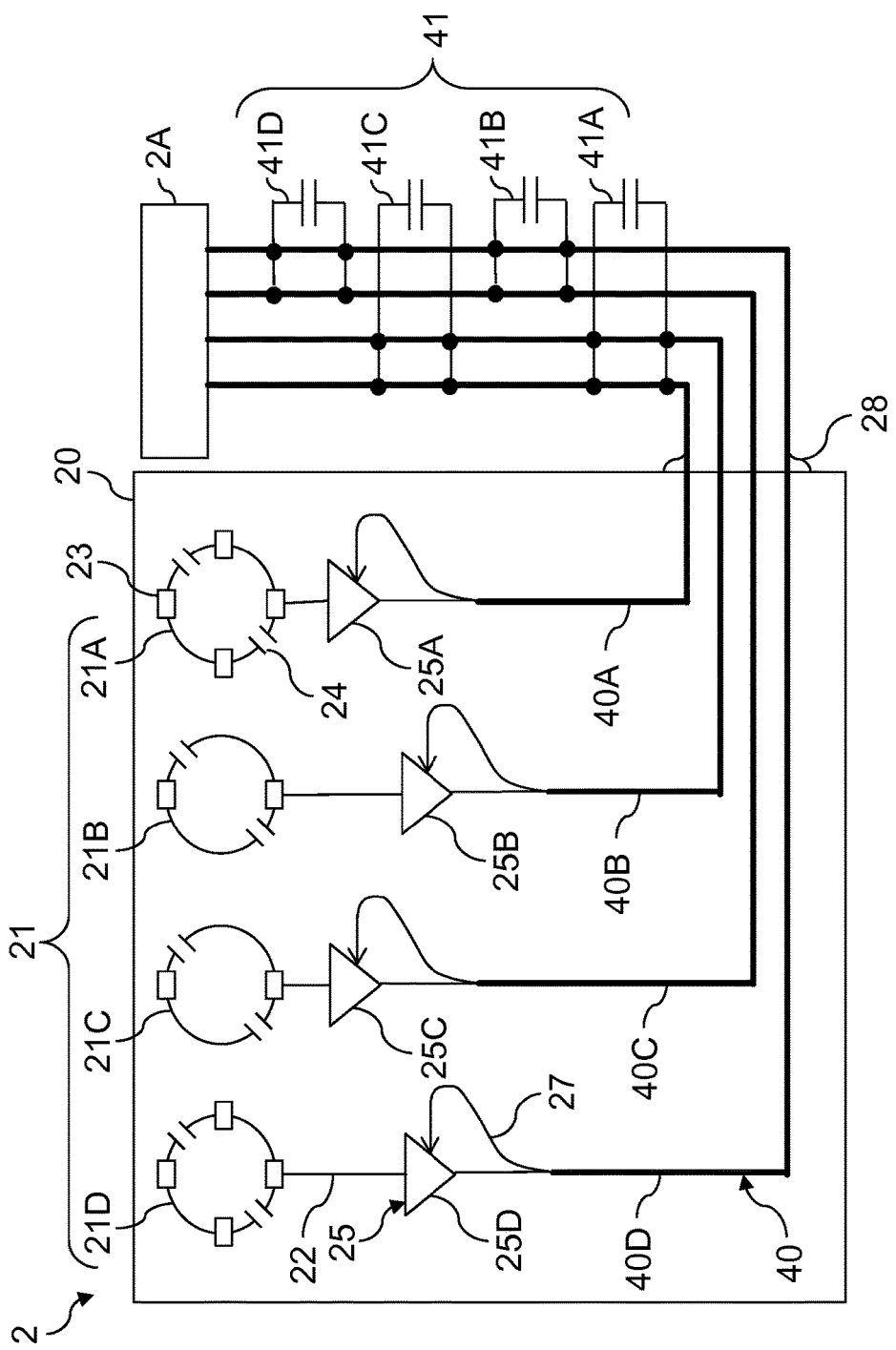
FIG. 2 is a view showing an example of detailed configuration of the RF coil unit shown in FIG. 1.

FIG. 2 is a view showing an example of detailed configuration of the RF coil unit 2 shown in FIG. 1.

The RF coil unit 2 is configured by connecting RF coil elements 21, housed by a casing 20, with the connector 2A through signal lines 22 of MR signals. Then, the RF coil elements 21 can be detached from and attached with the magnetic resonance imaging apparatus 1 by the connector 2A.

An arbitrary number of decoupling circuits 23 and capacitors 24 are connected to each RF coil element 21. The decoupling circuits 23 shift a resonance frequency of each RF coil element 21, in order to avoid coupling between the transmission RF coils and the reception RF coils when RF transmission signals are generated. On the other hand, the capacitors 24 are circuit elements for controlling a voltage peak in each RF coil element 21.

Each of the signal lines 22 of MR signals corresponding to the RF coil elements 21 is configured by an AC (Alternating Current) coaxial cable. Then, an amplifier 25 for amplifying MR signals is connected to each of the signal lines 22 of MR signals. Therefore, the RF coil unit 2 has the amplifiers 25 corresponding to the number of the RF coil elements 21. A power line 27 is connected to each amplifier 25. The power line 27 connects the amplifier 25 with a power supply.

Moreover, signal lines 28 for identifying an RF coil are connected to the casing 20 of the RF coil unit 2. From the signal lines 28 for identifying the RF coil, an identification signal of the RF coil unit 2 is output.

Figure 3:
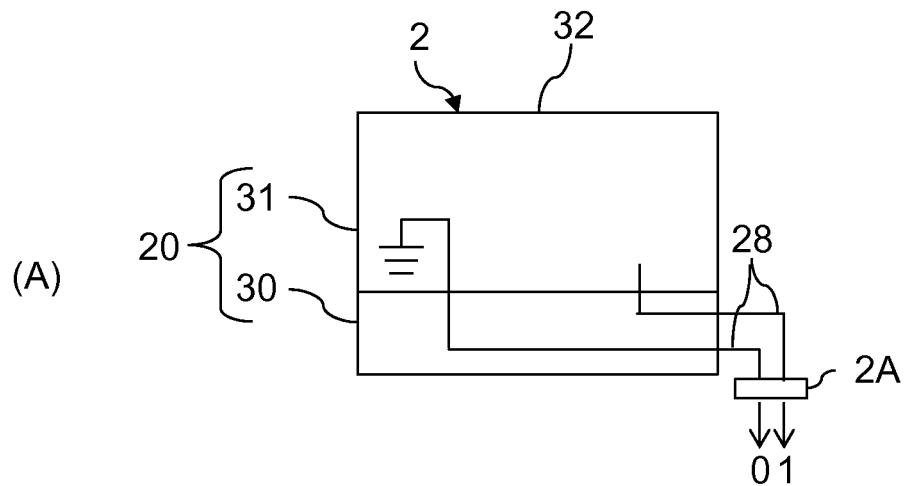
FIG. 3 is a view showing an example method of generating an identification signal of the RF coil unit.
Figure 3:
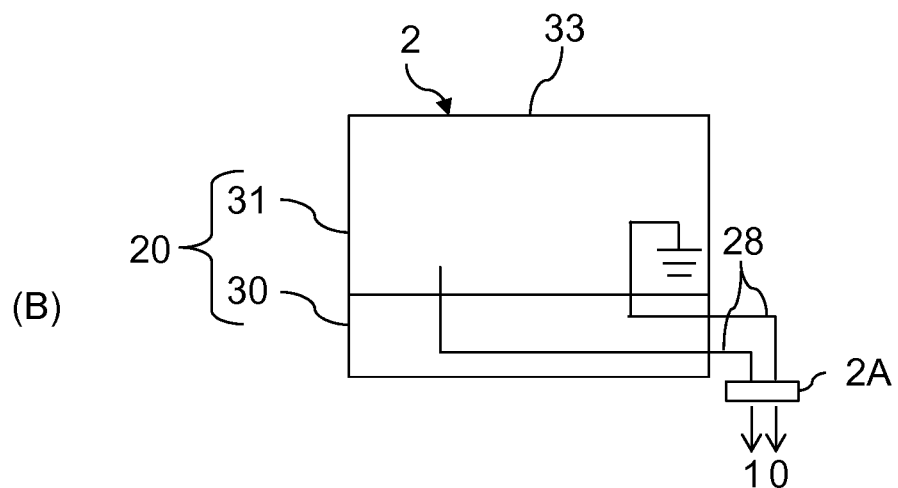

FIG. 3 is a view showing an example method of generating an identification signal of the RF coil unit 2.

The casing 20 which composes the RF coil unit 2 can be divided. FIGS. 3 (A) and (B) show an example that a coil-side casing 31 housing desired RF coil elements 21 can be chosen to be detached from and attached to a casing 30 in the connector 2A side. FIG. 3 (A) shows an example case of connecting the first casing 32 to the casing 30 in the connector 2A side. On the other hand, FIG. 3 (B) shows an example case of connecting the second casing 33 to the casing 30 in the connector 2A side.

As shown in FIG. 3, the casing 30 in the connector 2A side is connectable with the connector 2A by two signal lines 28 for identifying an RF coil. On the other hand, two terminals to be respectively connected with the two signal lines 28, for identifying the coil, of the casing 30 in the connector 2A side can be prepared in each of the first casing 32 in the coil side and the second casing 33 in the coil side.

Then, one of the two terminals included in each of the first casing 32 and the second casing 33 is connected to the ground. However, the signal line 28, for identifying the coil, corresponding to the grounded terminal of the first casing 32 is different from that of the second casing 33. Then, a voltage is applied to each of the two terminals of the casing 30 in the connector 2A side.

Then, the connector 2A side can receive a signal, for identifying each coil, whose polarity changes according to whether the first casing 32 has been connected to the casing 30 in the connector 2A side or the second casing 33 has been connected to the casing 30 in the connector 2A side. When the zero potential is denoted by 0 while the positive potential is denoted by 1, for example, the terminal connected to the ground can be denoted by 0 while the terminal unconnected to the ground can be denoted by 1. Therefore, it becomes possible to generate the signal, for identifying each coil, denoted using the two values of 0 and 1.

The signal line 28 for identifying the coil and the power line 27 for the amplifier 25 are bundled with the signal lines 22 of MR signals to compose a composite cable 40. Therefore, the cable 40 includes the signal lines 22 of MR signals, the power line 27 for the amplifier 25, and the signal line 28 for identifying the coil.

The number of the cables 40 may be the number of reception channels or transmission channels of the RF coil unit 2. However, signal lines 22 of MR signals corresponding to multi channels may be included in a common cable 40. Therefore, the number of the cables 40 does not necessarily agree with the number of the channels.

Moreover, the number of the RF coil elements 21 may not coincide with the number of the channels. In that case, a distribution-and-composition circuit of MR signals is provided in the RF coil unit 2. Specifically, the distribution-and-composition circuit of MR signals is connected with the output side of the RF coil elements 21 and the cables 40 whose number corresponds to the number of the channels are connected to the output side of the distribution-and-composition circuit. Therefore, when the number of the RF coil elements 21 does not agree with the number of the channels, the number of the cables 40 does not agree with the number of the RF coil elements 21 even when the cable 40 is provided for every channel.

Moreover, the RF coil elements 21 composing the RF coil unit 2 are directly or indirectly connected to the cables 40 corresponding to the channels.

Furthermore, the RF coil unit 2 includes balun circuits 41 to inhibit the influence of unbalanced currents. At least one balun circuit 41 of the balun circuits 41 is configured to suppress the influence of the unbalanced currents flowing into partial RF coil elements 21 among the RF coil elements 21 by making a part of the cables 40 pass through the balun circuit 41 in contact with or in non-contact with the balun circuit 41.

Suitably, the RF coil unit 2 includes the balun circuits 41 through which mutually different combinations of the cables 40 pass in contact with or in non-contact with the balun circuits 41, as illustrated. More specifically, at least two of the balun circuits 41 are arranged so that different combinations of the cables 40 pass through the two balun circuits 41 respectively in contact with or in non-contact with the two balun circuits 41. Note that, a same number of the cables 40 or different numbers of the cables 40 may pass through the two balun circuits 41 through which different combinations of the cables 40 pass.

Therefore, each cable 40 does not pass through all the balun circuits 41 but passes through only a part of the balun circuits 41. Accordingly, the electrical loads applied to the balun circuits 41 and the amount of heat generation in the balun circuits 41 can be distributed.

Further preferably, the RF coil units 2 have plural sets of the balun circuits 41 as described above through which mutually different combinations of the cables 40 pass in contact with or in non-contact with the balun circuits 41, as illustrated. In this case, each cable 40 passes multiple balun circuits 41. Thereby, the inhibition capability of the unbalanced currents can be maintained or raised with distributing the electrical loads applied to the balun circuits 41 and the amount of heat generation in the balun circuits 41.

FIG. 2 exemplifies the RF coil unit 2 having four channels. Specifically, the cable 40 is connected to each of the four RF coil elements 21. Then, each two cables 40 configure one group and the four cables 40 are separated into two groups.

Furthermore, the RF coil unit 2 includes two sets of the two balun circuits 41. Each group consisting of two cables 40 passes through the corresponding set of the two balun circuits 41. Therefore, the number of the balun circuits 41 is four. More specifically, the first and second cables 40A and 40B pass the first and third balun circuits 41A and 41C while the third and fourth cables 40C and 40D pass the second and fourth balun circuits 41B and 41D. As described above, the cables 40 can be separated into groups, and the balun circuits 41 which the cables 40 pass can be changed for each group.

Moreover, the amplifier 25 is connected to the signal line 22 of MR signals between the balun circuits 41 and the RF coil element 21 in each channel. Then, each amplifier 25 is arranged so that the sum of the circuit lengths between the RF coil elements 21 and the amplifiers 25 in one group becomes equal to that in another group. Specifically, the sum of the circuit length between the first RF coil element 21A and the first amplifier 25A, which correspond to the first channel, and the circuit length between the second RF coil element 21B and the second amplifier 25B, which correspond to the second channel, is equal to the sum of the circuit length between the third RF coil element 21C and the third amplifier 25C, which correspond to the third channel, and the circuit length between the fourth RF coil element 21D and the fourth amplifier 25D, which correspond to the fourth channel.

In other words, the balun circuits 41 can be arranged so that the sum of the circuit lengths, from the RF coil elements 21 to the amplifiers 25, of the signal lines 22 of MR signals passing each balun circuit 41 becomes equal. That is, a group of the cables 40 passing common balun circuits 41 can be determined so that the sum of the circuit lengths between the RF coil elements 21 and the amplifiers 25 becomes equal between the groups.

As described above, it becomes possible to distribute the electrical loads applied to the balun circuits 41 and the amount of heat generation in the balun circuits 41 more equally by making various conditions, about the signal lines 22 passing the balun circuits 41, equivalent.

Figure 4:
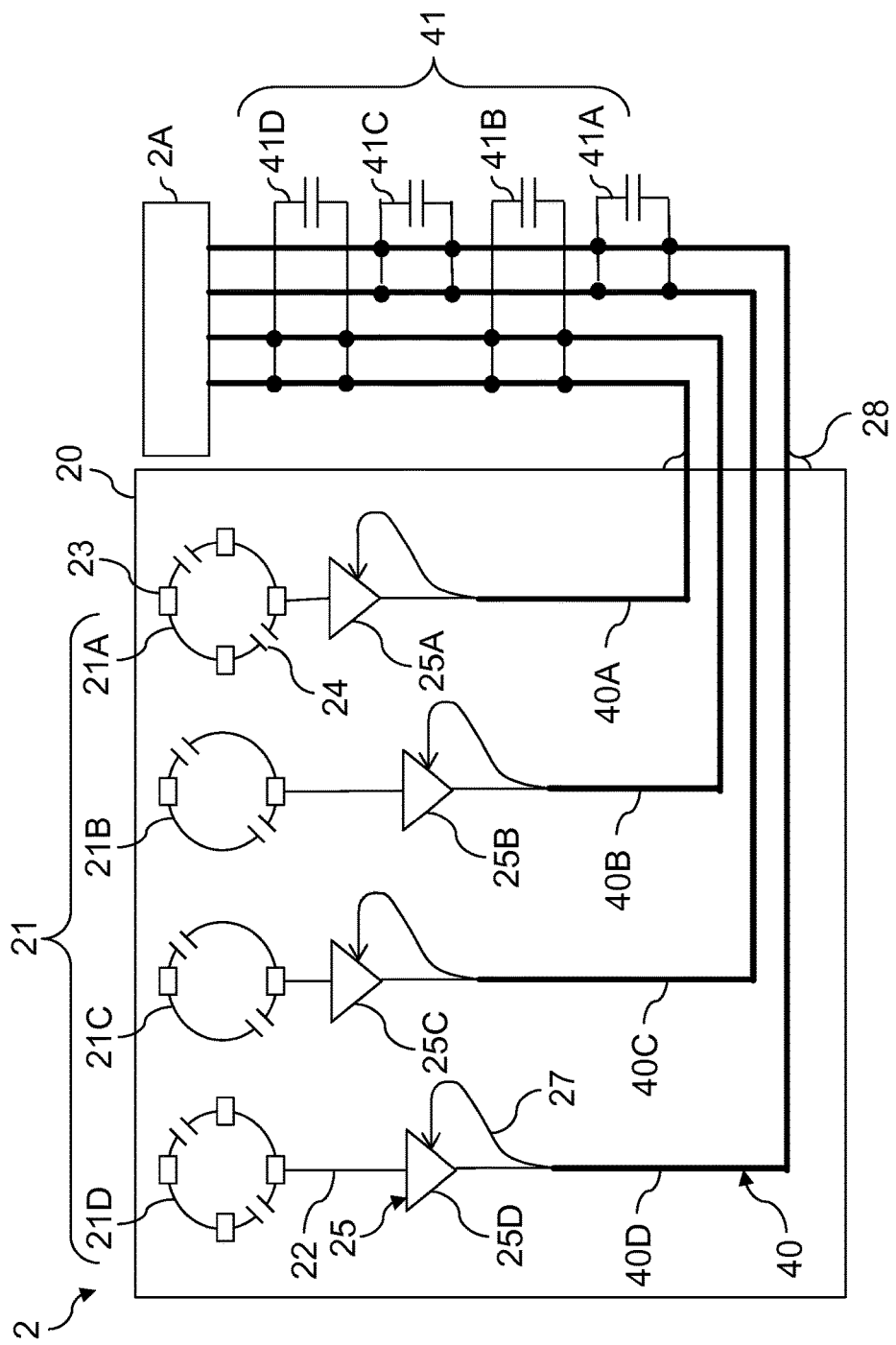
FIG. 4 is a view showing another example of detailed configuration of the RF coil unit shown in FIG. 1.

FIG. 4 is a view showing another example of detailed configuration of the RF coil unit 2 shown in FIG. 1.

The RF coil unit 2 exemplified in FIG. 4 is also an RF coil, having four channels, similar to the RF coil unit 2 exemplified in FIG. 2. Therefore, four RF coil elements 21A, 21B, 21C, and 21D and four amplifiers 25A, 25B, 25C, and 25D from the first to the fourth are included in the RF coil unit 2. Moreover, four balun circuits 41 are installed.

However, in the example shown in FIG. 4, a plurality of sets of the balun circuits 41 are arranged so that the sum of the circuit lengths from the balun circuit 41, nearest to the RF coil elements 21, to the amplifiers 25, of the signal lines 22 of MR signals passing each balun circuit 41 becomes equal. Specifically, the third and fourth cables 40C and 40D pass the first and third balun circuits 41A and 41C while the first and second cables 40A and 40B pass the second and fourth balun circuits 41B and 41D. Then, a circuit configuration of the RF coil unit 2 is determined so that the sum of the circuit lengths between the first balun circuit 41A, nearest to the third and fourth RF coil elements 21C and 21D, and the third and fourth amplifiers 25C and 25D becomes equal to the sum of the circuit lengths between the second balun circuit 41B, nearest to the first and second RF coil elements 21A and 21B, and the first and second amplifiers 25A and 25B.

Note that, a plurality of sets of the balun circuits 41 may be arranged so that the sum of the circuit lengths between the balun circuit 41, nearest to the RF coil elements 21, and the RF coil elements 21 becomes equal, instead of the sum of the circuit lengths between the balun circuit 41, nearest to the RF coil elements 21, and the amplifiers 25, or in addition to the sum of the circuit lengths between the balun circuit 41, nearest to the RF coil elements 21, and the amplifiers 25.

Besides the conditions about the circuit lengths of the signal lines 22 of MR signals, as exemplified in FIG. 2 and FIG. 4, other conditions may also be made equivalent between the balun circuits 41. For example, the balun circuits 41 can be arranged so that the sum of the areas of the RF coil elements 21 connected to the signal lines 22 of MR signals passing each balun circuit 41, the circuit length, of the power line 27 for the amplifier 25 passing each balun circuit 41, from the balun circuit 41 nearest to the RF coil element 21, to the amplifier 25, or the circuit length of the signal line 28 for identifying of the RF coil element 21 passing each balun circuit 41 becomes equal.

Especially, the power line 27 for the amplifier 25 is DC (Direct Current) and has an inductance component (L component). Accordingly, the longer the power line 27 for the amplifier 25 is, the more the power line 27 generates heat. Therefore, equalizing the circuit lengths of the power lines 27 for the amplifiers 25 between the balun circuits 41 makes it possible to equally distribute the amount of heat generation in the balun circuits 41.

Furthermore, one or both of the number of the decoupling circuits 23 and the number of the capacitors 24, installed in each RF coil element 21, may be also arrangement conditions of the balun circuits 41. Specifically, the plural balun circuits 41 can be arranged so that a value derived by dividing the sum of element lengths or areas of the RF coil elements 21, connected to the signal lines 22 of MR signals passing each balun circuit 41, by at least one of the sum of the numbers of the decoupling circuits 23 installed on the radio frequency coil elements 21 and the sum of the numbers of the capacitors 24, for inhibiting voltage peaks, installed on the radio frequency coil elements 21 becomes equivalent.

When the four RF coil elements 21A, 21B, 21C, and 21D have even element lengths and areas, when the number of the decoupling circuits 23 connected to each of the first RF coil element 21A and the fourth RF coil element 21D is four, and when the number of the decoupling circuits 23 connected to each of the second RF coil element 21B and the third RF coil element 21C is two, as shown in FIG. 2 and FIG. 4, for example, the four RF coil elements 21A, 21B, 21C, and 21D can be separated into the group consisting of the first and second RF coil elements 21A and 21B and the group consisting of the third and fourth RF coil elements 21C and 21D so that each sum of the numbers of the decoupling circuits 23 becomes six.

The above mentioned method of determining an arrangement of the plural balun circuits 41 is a theoretical method based on design values such as circuit lengths. However, an electrical load on each balun circuit 41 may be actually measured to determine an arrangement of the plural balun circuits 41 according to the measurement results so that the electrical loads can be distributed more evenly.

Then, each of the balun circuits 41 whose arrangement has been determined theoretically or experientially can be passed by a part of the plural cables 40 with or without contact. On the other hand, the remaining cables 40 can pass the balun circuits 41 in a different aspect, or can avoid passing the balun circuits 41.

Figure 5:
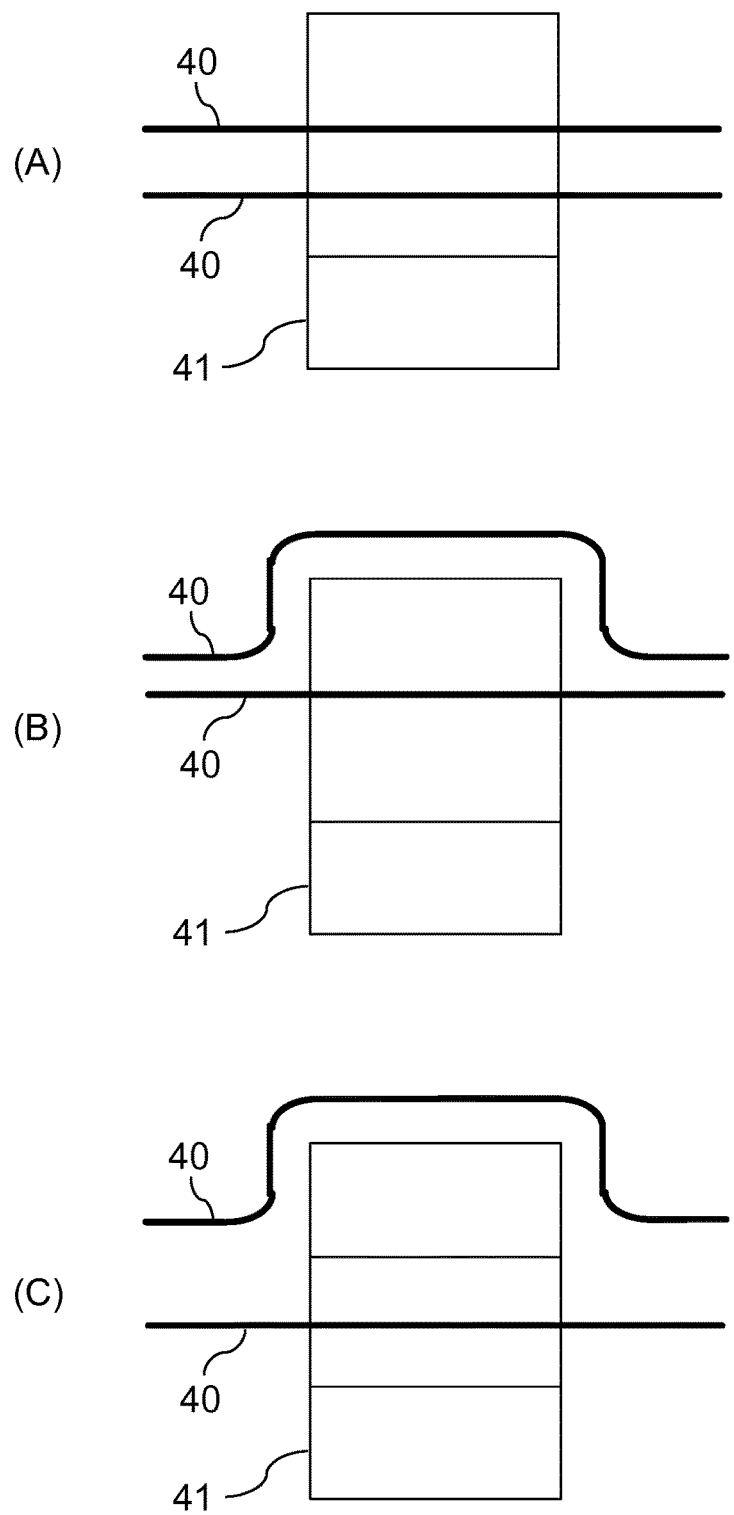
FIG. 5 shows transverse sections indicating configurations of the cables passing through each balun circuit shown in FIG. 2 or FIG. 4.

FIG. 5 shows transverse sections indicating configurations of the cables 40 passing through each balun circuit 41 shown in FIG. 2 or FIG. 4.

As shown in FIG. 5, the balun circuit 41 has a cylindrical structure. FIGS. 5 (A), (B) and (C) show methods by which a part of the plural cables 40 pass inside the balun circuit 41, having the cylindrical structure, with or without contact.

FIG. 5 (A) shows the case that at least one of the plural balun circuits 41 is configured so that a part of the cables 40 pass through the balun circuit 41 in contact with the balun circuit 41 while the other cables 40 pass through the balun circuit 41 in non-contact with the balun circuit 41. FIG. 5 (B) shows the case that at least one of the plural balun circuits 41 is configured so that a part of the cables 40 pass through the balun circuit 41 in contact with the balun circuit 41 while the other cables 40 do not pass through the balun circuit 41. That is, the other cables 40 pass outside the balun circuit 41. FIG. 5 (C) shows the case that at least one of the plural balun circuits 41 is configured so that a part of the cables 40 pass through the balun circuit 41 in non-contact with the balun circuit 41 while the other cables 40 do not pass through the balun circuit 41.

As exemplified in FIG. 5, embodiments of a cable 40 passing through the balun circuit 41 include the two ways. Under one way, the cable 40 passes through the balun circuit 41 with contacting the cable 40 with the balun circuit 41. Under the other way, the cable 40 passes through the balun circuit 41 without contacting the cable 40 with the balun circuit 41. Therefore, some of the plural cables 40 may pass inside the balun circuit 41 in the embodiment different from the embodiment of the other cables 40. Alternatively, some of the plural cables 40 may be guided inside the balun circuit 41 while the other cables 40 may be guided outside the balun circuit 41.

When the cable 40 passes inside the balun circuit 41, an unbalanced current flowing the cable 40 can be suppressed though the balun circuit 41 bears an electrical load. In this case, contacting the cable 40 with the balun circuit 41 can further raise deterrent effects of an unbalanced current flowing the cable 40 although the balun circuit 41 bears a larger electrical load. On the other hand, guiding the cable 40 outside the balun circuit 41 can avoid an electrical load on the balun circuit 41. Therefore, the aspect of the cable 40 which passes through the balun circuit 41 can be determined appropriately according to an electrical load estimated theoretically or experimentally and an unbalanced current to be suppressed Moreover, a part of plural cables 40 may pass through a single balun circuit 41 in non-contact with the balun circuit 41, another part of the cables 40 may pass through the balun circuit 41 in contact with the balun circuit 41, and the remaining cables 40 may not pass through the balun circuit 41. That is, a combination of the inside passage with contact, the inside passage without contact, and the outside passage of the cables 40 can be applied. In this case, a theoretical estimation of an electrical load put on the balun circuit 41 is complicated. Therefore, it is practical to experimentally determine an arrangement of the balun circuits 41 and passage embodiments of the cables 40.

As conditions for arranging the plural balun circuits 41 other than the above mentioned conditions, conditions depending on relations with wavelengths of RF signals can be mentioned. Specifically, it is important to arrange the balun circuits 41, the amplifiers 25, and the connector 2A so that any of a circuit length of from the connector 2A to each balun circuit 41 nearest to the connector 2A, a circuit length between each adjacent balun circuits 41 connected with each other and a circuit length from each amplifier 25 to the balun circuit 41 nearest to the amplifier 25 becomes not more than one tenth of a wavelength of RF signal. These conditions are derived from experimental rules in RF circuits.

As mentioned above, in the RF coil unit 2 and the magnetic resonance imaging apparatus 1, balun circuits 41 to be used are determined for each cable 40, including signal lines 22, 28 and/or a power line 27, or each group consisting of plural cables 40, according to the amounts of heat generation in the balun circuits 41 and/or a circuit configuration, instead of guiding all the cables 40 inside all the balun circuits 41.

For this reason, in the RF coil unit 2 and the magnetic resonance imaging apparatus 1, electrical loads bore by the balun circuits 41 and amounts of heat generation in the balun circuits 41 can be distributed. That is, the balun circuits 41 can produce heats more evenly.

Second Embodiment

Figure 6:
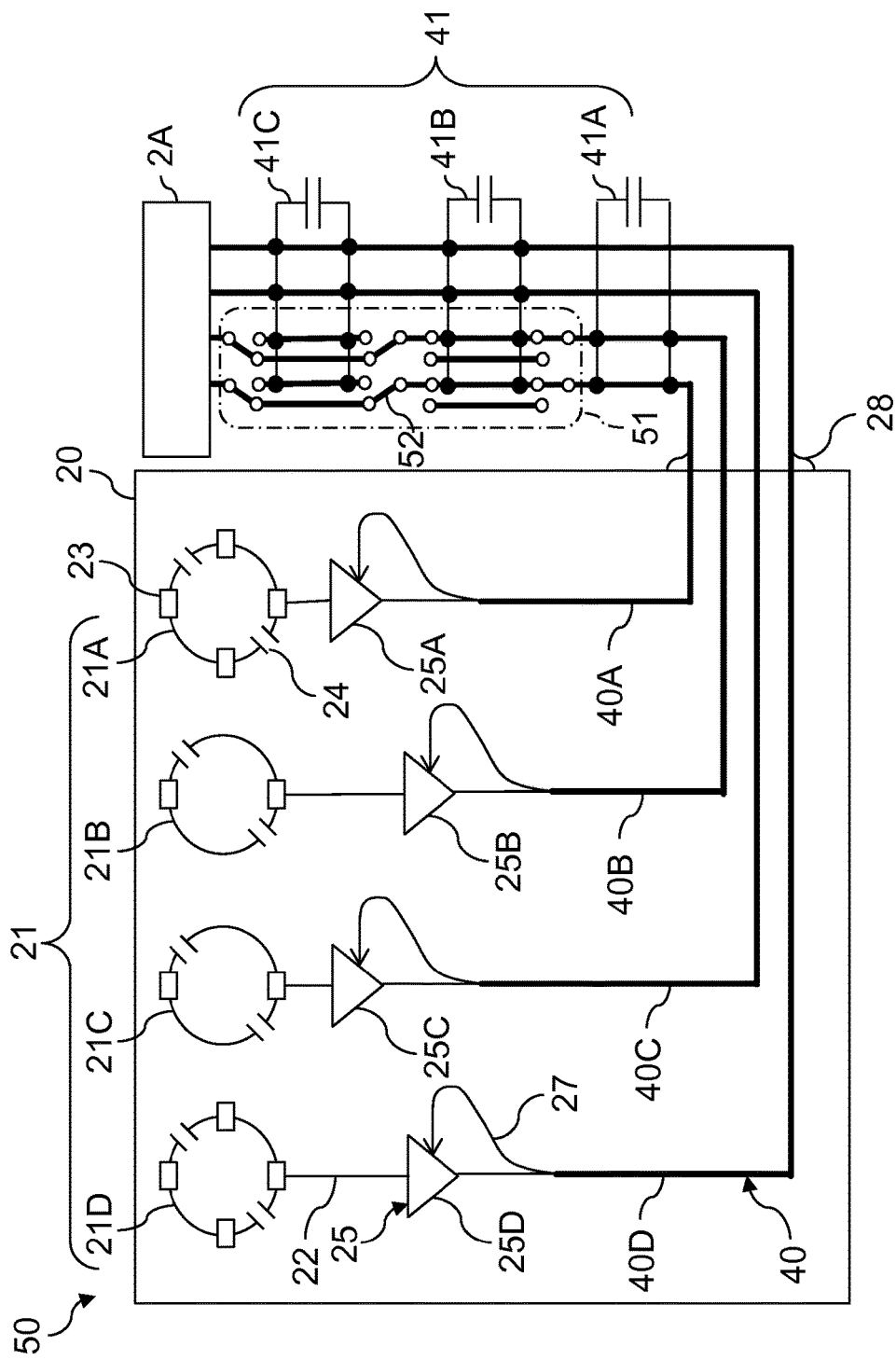
FIG. 6 is a structural view showing an RF coil unit according to the second embodiment of the present invention.
Figure 7:
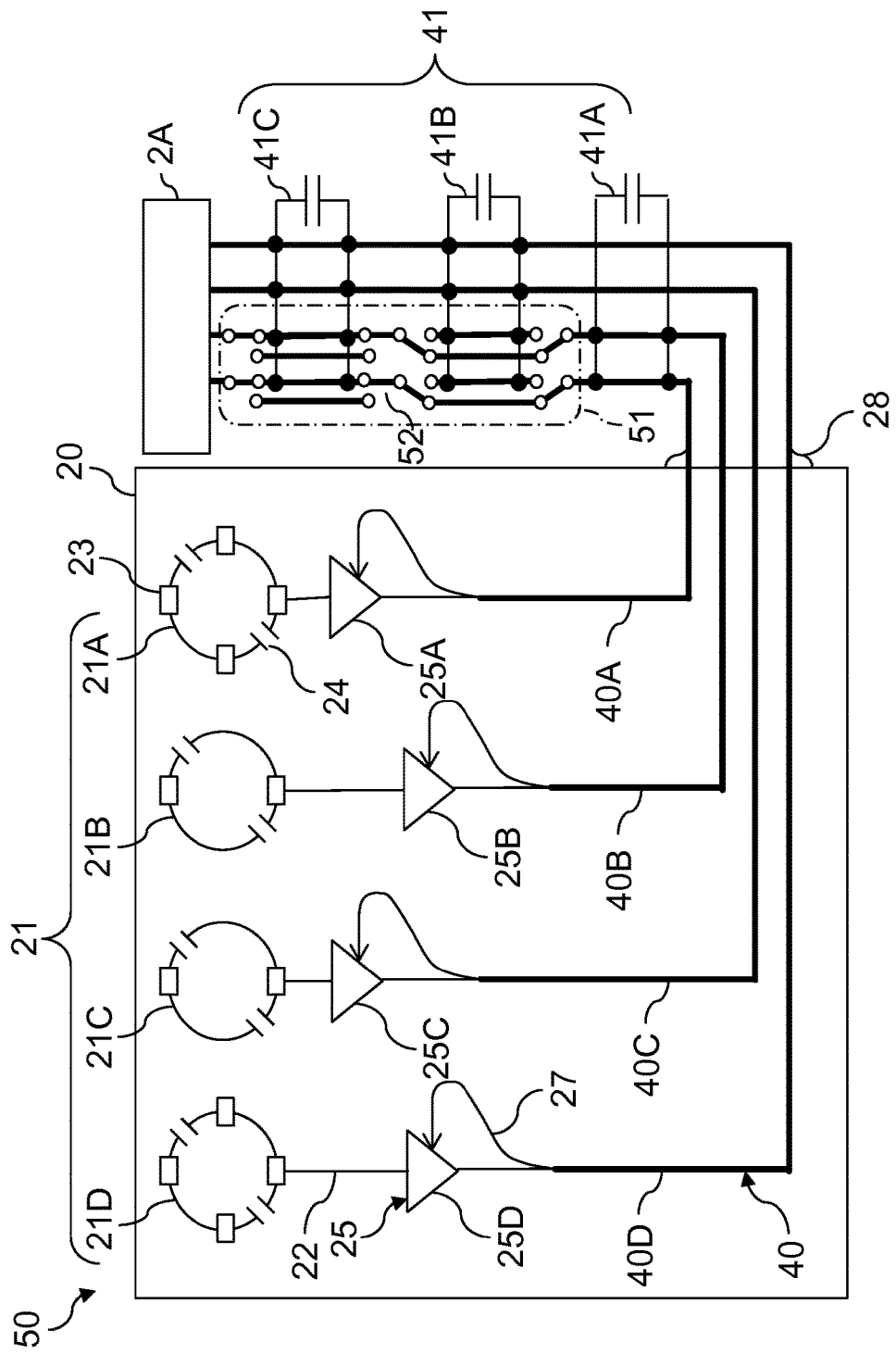
FIG. 7 is a view showing the state that the switches of the switching circuit shown in FIG. 6 have been switched.

FIG. 6 is a structural view showing an RF coil unit according to the second embodiment of the present invention. FIG. 7 is a view showing the state that the switches of the switching circuit shown in FIG. 6 have been switched.

An RF coil unit 50 in the second embodiment shown in FIG. 6 is different from the RF coil unit 2 in the first embodiment in point of providing a switching circuit 51 which changes the number of cables 40 passing through at least one balun circuit 41, inside which a part of plural cables 40 pass, or at least another one balun circuit 41. Since other configurations and functions of the RF coil unit 50 in the second embodiment do not differ from those of the RF coil unit 2 in the first embodiment substantially, the same signs are used to the same elements and the explanations thereof are omitted.

In the example shown in FIG. 6, the RF coil unit 50 has three balun circuits 41 in the order of the first balun circuit 41A, the second balun circuit 41B, and the third balun circuit 41C from the RF coil element 21 side toward the connector 2A side. Furthermore, the switching circuit 51, which changes the number of the cables 40 passing inside the second balun circuit 41B and the third balun circuit 41C, is installed.

The switching circuit 51 can be composed by connecting plural switches 52, using PIN (p-intrinsic-n) diodes etc., on the cables 40 as illustrated. The switching circuit 51 may be surely composed by connecting switches to the balun circuit 41 sides.

In the shown example, the second balun circuit 41B and the third balun circuit 41C are configured so that whether the first and second cables 40A and 40B pass through the second balun circuit 41B and the third balun circuit 41C or not can be selected by switching the switches 52. FIG. 6 shows the state that the first and second cables 40A and 40B pass through the second balun circuit 41B while the first and second cables 40A and 40B do not pass through the third balun circuit 41C. Meanwhile, FIG. 7 shows the state that the first and second cables 40A and 40B pass through the third balun circuit 41C while the first and second cables 40A and 40B do not pass through the second balun circuit 41B.

On the other hand, the first balun circuit 41A is configured so that only the first and second cables 40A and 40B pass through the first the balun circuit 41A. Moreover, the second balun circuit 41B and the third balun circuit 41C are configured so that the third and fourth cables 40C and 40D pass through the second balun circuit 41B and the third balun circuit 41C.

Therefore, whether the first and second cables 40A and 40B pass through the second balun circuit 41B or the third balun circuit 41C can be switched by switching the switches 52 composing the switching circuit 51. Thereby, all the cables 40A, 40B, 40C and 40D can pass through two balun circuits 41 respectively. On the other hand, the number of the cables 40 which pass through the second balun circuit 41B and the number of the cables 40 which pass through the third balun circuit 41C can be increased and decreased.

As a result, the number of the cables 40 which pass through the second balun circuit 41B and the third balun circuit 41C can be changed according to conditions. Consequently, the electrical loads bore by the balun circuits 41 and the amounts of heat generation in the balun circuits 41 can be distributed appropriately according to conditions.

Figure 8:
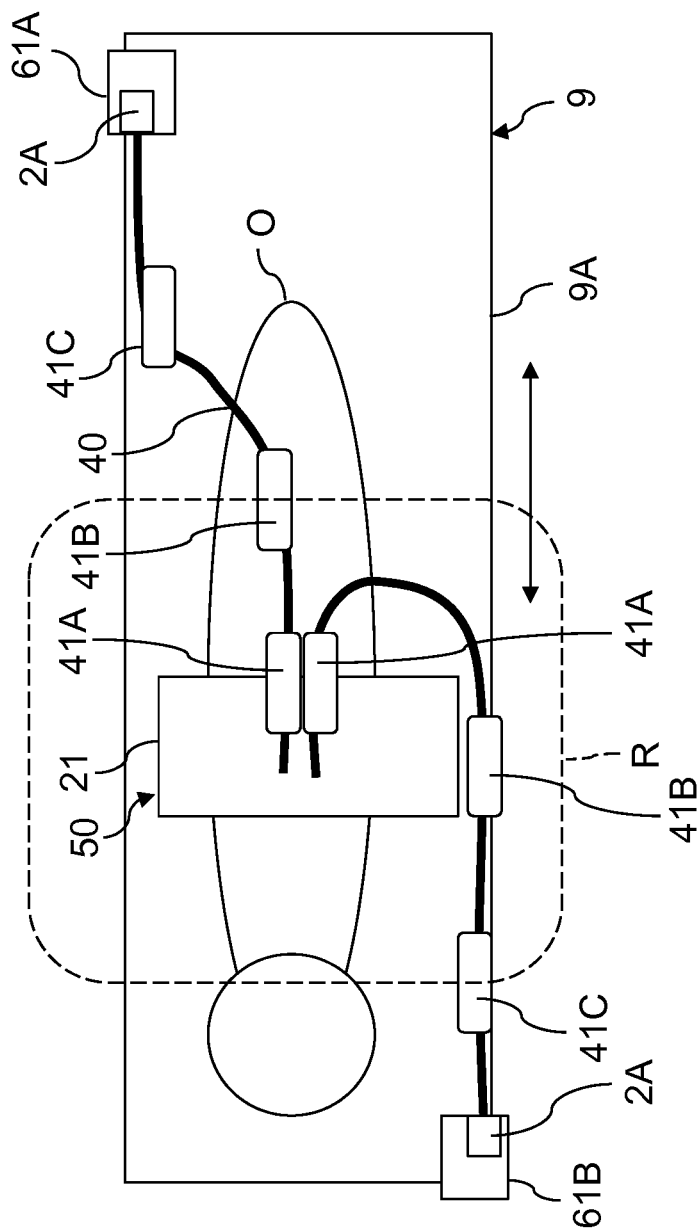
FIG. 8 is a view showing the state that the RF coil unit shown in FIG. 6 has been attached to each of connector ports prepared on the top plate of the bed.

FIG. 8 is a view showing the state that the RF coil unit 50 shown in FIG. 6 has been attached to each of connector ports prepared on the top plate 9A of the bed 9.

Plural connector ports are occasionally installed on the top plate 9A of the bed 9. In that case, it may be possible to attach the connector 2A of the RF coil unit 50 with each connector port. In the shown example, the first connector port 61A and the second connector port 61B are installed on the top plate 9A.

A switch for recognizing that the connector 2A of the RF coil unit 50 has been connected is installed with each of the first connector port 61A and the second connector port 61B. For this reason, the control system 10 of the magnetic resonance imaging apparatus 1 can recognize whether the connector 2A of the RF coil unit 50 has been connected with the first connector port 61A or the second connector port 61B.

Thus, when a connecting target of the connector 2A of the RF coil unit 50 is selectable, the unbalanced currents arising in the cables 40 change according to whether the connector 2A of the RF coil unit 50 has been connected with the first connector port 61A or the second connector port 61B. Therefore, the amount of heat generation in each balun circuit 41A, 41B, and 41C also changes.

Specifically, the heat value of the balun circuit 41 increases near the RF coil elements 21 and around a boundary line of transmission region R of RF signals. On the other hand, the heat value of the balun circuit 41 decreases at a position away from the RF coil element 21 and the boundary line of the transmission region R of RF signals.

As a specific example, when the connector 2A of the RF coil unit 50 has been connected to the first connector port 61A, the heat values of the first balun circuit 41A near the RF coil element 21 and the second balun circuit 41B around the boundary of the transmission region R of RF signals become large. On the contrary, the heat value of the third balun circuit 41C becomes small. Therefore, it is suitable to increase the number of the cables 40 passing through the third balun circuit 41C, and to decrease the number of the cables 40 passing through the first balun circuit 41A and the second balun circuit 41B.

On the other hand, when the connector 2A of the RF coil unit 50 has been connected to the second connector port 61B, the heat values of the first balun circuit 41A near the RF coil element 21 and the third balun circuit 41C around the boundary of the transmission region R of RF signals become large. On the contrary, the heat value of the second balun circuit 41B becomes small. Therefore, it is suitable to increase the number of the cables 40 passing through the second balun circuit 41B, and to decrease the number of the cables 40 passing through the first balun circuit 41A and the third balun circuit 41C.

That is, the balun circuit 41 around the boundary of the transmission region R of RF signals changes between the second balun circuit 41B and the third balun circuit 41C according to whether the connector 2A of the RF coil unit 50 has been connected with the first connector port 61A or the second connector port 61B.

Accordingly, the switching circuit 51 can be configured to change the number of the cables 40 passing through the balun circuits 41 according to the transmission region R of RF signals. Specifically, the switching circuit 51 can be configured to change the number of the cables 40 according to the identification information of the connector port 61A or 61B with which the cables 40 are connected through the connector 2A. The identification information of the connector port 61A or 61B with which the cables 40 are connected can be given to the switching circuit 51 as a signal from the switch installed on the first connector port 61A or the second connector port 61B, or as a control signal from the control system 10.

As another example, the switching circuit 51 may be configured to change the number of the cables 40 according to a movement distance of the top plate 9A of the bed 9 with which the RF coil elements 21 are attached. In that case, the movement distance of the top plate 9A is given from the bed 9 or the control system 10 to the switching circuit 51.

As another example, the switching circuit 51 may be configured to change the number of the cables 40 according to information specifying an imaging region or an imaging part of an object O using the RF coil elements 21. In that case, information specifying an imaging region or an imaging part is given from the control system 10 to the switching circuit 51.

That is, positional relationship between a position of each balun circuit 41 and a transmission region R of RF signals can be predicted based on a single or plural conditions, such as identification information of each connector port 61A and 61B with which the cables 40 are connected, a movement distance of the top plate 9A, and/or an imaging area. Then, the number of the cables 40 passing through each balun circuit 41 can be switched automatically based on the predicted position, relative to the transmission region R of RF signals, of each balun circuit 41. Moreover, the number of the balun circuits 41 through which each cable 40 passes can be also changed.

More specifically, a table in which each switching condition of the switching circuit 51 is related with a single or plural conditions, such as identification information of each connector port 61A and 61B with which the cables 40 are connected, a movement distance of the top plate 9A, and an imaging area can be prepared. Thereby, the switching circuit 51 can be controlled according to the table. The determination and the control of the switching condition of the switching circuit 51 based on the table may be performed autonomously by the switching circuit 51 which acquires necessary information from the control system 10 or the bed 9. Alternatively, the control system 10 may acquire necessary information to perform the determination and the control of the switching condition of the switching circuit 51 based on the table.

Such control of the switching circuit 51 can be performed even when the connector ports 61A and 61B cannot be chosen as a connection target of the cables 40. That is, since a transmission region R of RF signals may change according to imaging conditions, such as a movement distance of the top plate 9A, an imaging region, and an imaging part, the switching circuit 51 can be controlled according to these imaging conditions.

The RF coil unit 50 in the second embodiment as mentioned above is to adjust effectively of the respective balun circuits 41 actively according to use conditions.

For this reason, the RF coil unit 50 in the second embodiment can attain flexibility in use conditions, such as a connected connector port, an imaging region, and a movement distance of the top plate, differently from the RF coil unit 2 in the first embodiment which suppresses heating values in the balun circuits 41 by adding restrictions to use conditions. Surely, electrical loads on the balun circuits 41 and heating values from the balun circuits 41 can be also distributed in the RF coil unit 50 in the second embodiment, similarly to the RF coil unit 2 in the first embodiment.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A radio frequency (RF) coil unit comprising:
cables corresponding to channels;
RF coil elements directly or indirectly connected to said cables; and
at least two balun circuits configured to suppress influence of unbalanced currents flowing into partial RF coil elements out of said RF coil elements, a first set of said cables passing through a first balun circuit out of said at least two balun circuits while a second set of said cables passes through a second balun circuit out of said at least two balun circuits, the first set being different from the second set.

2. The radio frequency coil unit of claim 1, wherein:
said balun circuits are arranged at positions such that a summation of circuit lengths of signal lines for RF signals included in cables passing through each balun circuit become equivalent when said balun circuits are arranged at said positions, the circuit lengths being measured from corresponding RF coil elements to RF amplifiers installed on the signal lines.

3. The radio frequency coil unit of claim 1, wherein said balun circuit sets are arranged at positions such that a summation of circuit lengths of signal lines for RF signals included in cables passing through each balun circuit become equivalent when said balun circuit sets are arranged at said positions, the circuit lengths being measured from a balun circuit, closest to respectively RF coil elements, to corresponding RF coil elements or amplifiers installed on the signal lines.

4. The radio frequency coil unit of claim 1, wherein:
said balun circuits are arranged at positions such that a summation of areas of RF coil elements connected with signal lines for RF signals included in cables passing through each balun circuit become equivalent when said balun circuits are arranged at said positions.

5. The radio frequency coil unit of claim 1, wherein:
said balun circuits are arranged at positions such that values become equivalent when said balun circuits are arranged at said positions, the values being derived by dividing a summation of element lengths or areas of RF coil elements connected with signal lines for RF signals included in cables passing through each balun circuit, the summation being divided by at least one of (a) a quantity of decouple circuits installed on the RF coil elements connected with the signal lines and (b) a quantity of capacitors for suppressing voltage peaks, the capacitors being installed on the RF coil elements connected with the signal lines.

6. The radio frequency coil unit of claim 1, further comprising:
amplifiers installed on signal lines of RF signals corresponding to said RF coil elements, said amplifiers amplifying the RF signals,
wherein said balun circuits are arranged at positions such that a circuit length of each power line for an amplifier included in cables passing through each balun circuit become equivalent when said balun circuits are arranged at said positions, the circuit length being measured from a balun circuit closest to a corresponding RF coil element to the amplifier.

7. The radio frequency coil unit of claim 1, wherein:
said balun circuits are arranged at positions such that a circuit length of a signal line for identifying a RF coil included in cables passing through each balun circuit become equivalent when said balun circuits are arranged at said positions.

8. The radio frequency coil unit of claim 1, further comprising:
amplifiers installed on signal lines of RF signals corresponding to said RF coil elements, said amplifiers amplifying the RF signals; and
a connector configured to attach and detach said RF coil elements to a magnetic resonance imaging apparatus,
wherein said balun circuits, said amplifiers, and said connector are arranged at positions such that each of a first circuit length, a second circuit length and a third circuit length become not more than one tenth of a wavelength of an RF signal being passed therethrough, the first circuit length being measured from said connector to a balun circuit closest to said connector, the second circuit length being the length between adjacent balun circuits connected with each other, the third circuit length being the length from said amplifiers to balun circuits closest to said amplifiers.

9. The radio frequency coil unit of claim 1, wherein:
a further part of the part of said cables passes through said at least one of said balun circuits in contact with said at least one of said balun circuits while another further part of the part of said cables passes through said at least one of said balun circuits in non-contact with said at least one of said balun circuits.

10. The radio frequency coil unit of claim 1, wherein:
a further part of the part of said cables passes through said at least one of said balun circuits in contact with said at least one of said balun circuits while another further part of the part of said cables does not pass through said at least one of said balun circuits.

11. The radio frequency coil unit of claim 1, wherein:
a further part of the part of said cables passes through said at least one of said balun circuits in non-contact with said at least one of said balun circuits while another further part of the part of said cables does not pass through said at least one of said balun circuits.

12. The radio frequency coil unit of claim 1, further comprising:
a switching circuit configured to change a number of cables passing through the at least one or at least another one of said balun circuits.

13. The radio frequency coil unit of claim 12, wherein:
said switching circuit is configured to change the number of passing-through cables according to a transmission region of a RF signal.

14. The radio frequency coil unit of claim 12, wherein:
said switching circuit is configured to change the number of passing-through cables according to identification information of a connector port connected with said cables.

15. The radio frequency coil unit of claim 12, wherein:
said switching circuit is configured to change the number of passing-through cables according to a movement distance of a top plate of a patient bed, said RF coil elements being installed with the top plate.

16. The radio frequency coil unit of claim 12, wherein:
said switching circuit is configured to change the number of passing-through cables according to specification information of an imaging region or an imaging part of an object using said RF coil elements.

17. The radio frequency coil unit of claim 1, wherein:
a number of cables in the first cable set is same as a number of cables in the second cable set.

18. The radio frequency coil unit of claim 1, wherein:
a number of cables in the first cable set is different from a number of cables in of the second cable set.

19. The magnetic resonance imaging apparatus of claim 1 further comprising:
an imaging system configured to perform magnetic resonance imaging using said RF coil unit.

* * * * *